US008481982B2

(12) United States Patent
Johnson et al.

(10) Patent No.: US 8,481,982 B2
(45) Date of Patent: Jul. 9, 2013

(54) ENERGY EMITTING TREATMENT DEVICE

(76) Inventors: Scot L Johnson, Tampa, FL (US); Daryl L Johnson, Pompano Beach, FL (US)

(*) Notice: Subject to any disclaimer, the term of this patent is extended or adjusted under 35 U.S.C. 154(b) by 185 days.

(21) Appl. No.: 12/857,797

(22) Filed: Aug. 17, 2010

(65) Prior Publication Data
US 2011/0037002 A1 Feb. 17, 2011

Related U.S. Application Data

(60) Provisional application No. 61/274,412, filed on Aug. 17, 2009.

(51) Int. Cl.
*G21K 5/04* (2006.01)

(52) U.S. Cl.
USPC ............ 250/493.1; 356/51; 250/504 R; 607/1

(58) Field of Classification Search
USPC ......... 250/493.1, 494.1, 503.1; 356/51; 607/1
See application file for complete search history.

(56) References Cited

U.S. PATENT DOCUMENTS

| | | | |
|---|---|---|---|
| 5,843,143 A | 12/1998 | Whitehurst | |
| 6,145,743 A * | 11/2000 | Dvorkis et al. | 235/462.01 |
| 6,171,332 B1 | 1/2001 | Whitehurst | |
| 6,461,866 B1 | 10/2002 | Whitehurst | |
| 6,626,932 B2 | 9/2003 | Whitehurst | |
| 6,645,230 B2 | 11/2003 | Whitehurst | |
| 7,897,907 B1 * | 3/2011 | Waters et al. | 250/214 R |
| 2002/0029071 A1 | 3/2002 | Whitehurst | |
| 2002/0035386 A1 | 3/2002 | Whitehurst | |
| 2002/0138120 A1 | 9/2002 | Whitehurst | |
| 2003/0019934 A1 * | 1/2003 | Hunter et al. | 235/462.2 |
| 2005/0051523 A1 * | 3/2005 | Legge et al. | 219/121.83 |
| 2007/0038269 A1 | 2/2007 | Whitehurst | |
| 2009/0054953 A1 | 2/2009 | Whitehurst | |
| 2010/0292951 A1 * | 11/2010 | Gaertner et al. | 702/135 |

FOREIGN PATENT DOCUMENTS

| | | |
|---|---|---|
| KR | 10-0787874 B1 | 12/2007 |
| KR | 10-2010-0010799 A | 2/2010 |
| WO | WO 2005-074776 A1 | 8/2005 |
| WO | WO 2008/017101 A1 | 2/2008 |
| WO | WO 2010-011024 A2 | 1/2010 |
| WO | WO 2010-061620 A1 | 6/2010 |

OTHER PUBLICATIONS

Korean Intellectual Property Office, PCT Notification of Transmittal of the International Search Report and the Written Opinion of the International Searching Authority, or the Declaration, PCT/US2011/047984, Apr. 24, 2012, Republic of Korea.

The International Bureau of WIPO, PCT International Preliminary Report on Patentability, International application No. PCT/US2011/047984, Feb. 19, 2013, Switzerland.

* cited by examiner

*Primary Examiner* — Nicole Ippolito
(74) *Attorney, Agent, or Firm* — The Compton Law Firm, P.C.; Scott Compton

(57) ABSTRACT

In one aspect, the present application is directed to a radiant energy emitting device. The radiant energy emitting device comprises (A) an outer housing including at least one aperture there through, the housing being operationally configured to (1) receive and contain radiant energy therein, and (2) emit radiant energy out through the aperture to a target surface; (B) an energy emission means; and (C) a sensor means disposed about the aperture of the housing, the sensor means being in communication with the energy emission means and operationally configured to detect the spatial relationship between the sensor means and the target surface, said spatial relationship determining activation of the energy emission means.

21 Claims, 11 Drawing Sheets

ENERGY EMITTING TREATMENT DEVICE

CROSS-REFERENCE TO RELATED APPLICATIONS

The application is entitled to the benefit of the filing date of the prior-filed provisional application No. 61/274,412, filed on Aug. 17, 2009.

STATEMENT REGARDING FEDERALLY SPONSORED RESEARCH OR DEVELOPMENT

Not applicable.

FIELD OF THE APPLICATION

The application relates generally to a radiant energy emitting treatment device for transmitting radiant energy to a target surface.

BACKGROUND

The concept of activating, deactivating, or limiting the primary function of a device according to its environment using sensing technology is decades old. Examples include (1) garage door openers whose door-closing cycle is limited either by infrared ("IR") beam detection of objects within the path of a closing garage door or by surges in the power consumed by the door-closing motor, and (2) light emitting devices such as outdoor floodlights with infrared detectors capable of sensing the presence of object(s) to activate/deactivate the floodlight. Over the years, various medical devices have incorporated similar sensing technologies to assist in gauging the proximity of a device to a target surface such as human tissue. However, medical devices using decades old sensing technology are subject to risk of producing unintended operation. For example, a typical heating lamp incorporating a proximity sensor comprising an infrared emitter and infrared-sensitive detector has an aperture or face of about two inches by four inches configured for emitting radiant heat energy from the lamp. With such lamps, the aperture must not be placed in direct contact with a patient, whereby the lamp utilizes its infrared sensor to bring the lamp to within an acceptable proximity of the target surface for desired operation. However, the infrared proximity sensor of such devices may not recognize a protruding non-flat surface, such as a person's nose, due to the requirement of reflection for proper sensor operation, thereby bringing the nose too close to the aperture and potentially causing a burn. In another instance, an infrared sensor may be brought too close to the skin, to within a range known as a "blind-spot," a range directly in front of the sensor where the sensor cannot detect the skin surface due to the geometric requirements of infrared reflection sensing. As a result, the device may incorrectly identify a properly spaced surface and allow radiant heat exposure to occur, potentially burning a target patient.

Improvements in medical devices are always desired. Thus, what is desired is an energy emitting treatment device with a sensor means for detecting a target surface to be irradiated, the device incorporating one or more of the following characteristics: (1) a sensor means effective to sense a target surface about an entire aperture as opposed to one point or a plurality of points, (2) a sensor means allowing radiant energy to pass unhindered or unattenuated out from the device, (3) a sensor means that does not require an aperture to sense a target surface, (4) a sensor means that does not operate on the principles of reflection, e.g. infrared light reflecting off a target surface, (5) a sensor means that may be programmed to sense particular surfaces rather than any surface within the device's field, (6) a sensor means not requiring a minimum distance between a sensor of the device and a target surface in order for target surface detection to occur, and (7) a sensor means that is resistant to electromagnetic radiation about a spectrum from less than ultraviolet wavelengths to greater than infrared wavelengths.

SUMMARY

The present application is directed to a radiant energy emitting device. The radiant energy emitting device comprises (A) an outer housing including at least one aperture there through, the housing being operationally configured to (1) receive and contain radiant energy therein, and (2) emit radiant energy out through the aperture to a target surface; (B) an energy emission means; and (C) a sensor means disposed about the aperture of the housing, the sensor means being in communication with the energy emission means and operationally configured to detect the spatial relationship between the sensor means and the target surface, said spatial relationship determining activation of the energy emission means.

The present application is also directed to a device for emitting radiant energy onto a target surface, comprising (A) an outer housing including at least one aperture there through; (B) an energy source for generating radiant energy, the energy source being in communication with the housing; (C) an activation means in communication with the energy source; and (D) a sensor means disposed about the perimeter of the aperture of the housing, the sensor means being in communication with the activation means and operationally configured to detect the spatial relationship between the sensor means and the target surface, said spatial relationship determining operation of the activation means; wherein the housing is operationally configured to emit radiant energy out through the aperture to the target surface.

The present application is also directed to a method for delivering radiant energy to a target surface while preventing unintended radiant energy emission, comprising (A) providing a radiant energy emitting device, comprising (1) an outer housing including at least one aperture there through, the housing being operationally configured to (i) receive and contain radiant energy therein, and (ii) emit radiant energy out through the aperture to a target surface; (2) an energy emission means; and (3) a sensor means disposed about the aperture of the housing, the sensor means being in communication with the energy emission means and operationally configured to detect the spatial relationship between the sensor means and the target surface, said spatial relationship determining activation of the energy emission means; (B) directing the device toward a target surface until the sensor means detects the spatial relationship between the sensor means and the target surface; and (C) activating the energy emission means for delivering radiant energy to the target surface.

BRIEF DESCRIPTION

Figure 1:
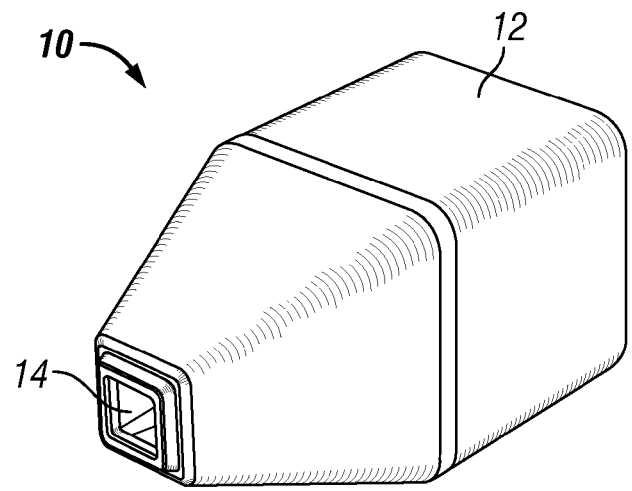
FIG. 1 is a perspective view of an embodiment of the present energy emitting treatment device.

It has been discovered that a radiant energy emitting device may be provided for directing radiant energy to a target surface area. The device suitably includes a sensor means operationally configured to activate a radiant energy source of the device as determined by the spatial relationship between the sensor and a target surface. Once the sensor of the device draws to within a predetermined proximity of a target surface, the energy source may be activated to emit radiant energy from the device in a manner effective to limit radiant energy exposure to the target surface area. In operation, the sensor means is effective to provide a device operationally configured to (1) sense substantially an entire target surface about an aperture as opposed to sensing at one point or a plurality of points about an aperture, (2) allow radiant energy to pass unhindered out from the device, (3) detect a target surface without using an aperture to sense the target surface, (4) operate on the principles other than reflection including infrared light reflecting off a target surface, (5) be programmed to sense particular surfaces rather than any surface within the device's sensing field, (6) detect the presence of a target surface without being limited by a minimum distance requirement between the sensor of the device and a target surface for detection of the target surface, and (7) resist electromagnetic radiation about a spectrum from less than ultraviolet wavelengths to greater than infrared wavelengths. Heretofore, such a desirable achievement has not been considered possible, and accordingly, the system and method of this application measure up to the dignity of patentability and therefore represents a patentable concept.

Before describing the invention in detail, it is to be understood that the present device, system, and method are not limited to particular embodiments. It is also to be understood that the terminology used herein is for the purpose of describing particular embodiments only, and is not intended to be limiting. As used in this specification and the appended claims, the term "radiant" or "radiant energy" is defined as the total electromagnetic energy emitted from an energy source in the form of electromagnetic waves intended to affect a target surface. Herein, the term "light" refers to radiant energy including the ultraviolet (UV), infrared (IR) and visible ranges of the electromagnetic radiation spectrum, and the term "visible light" refers to radiant energy in the visible range of the electromagnetic radiation spectrum. The phrase "target surface" refers to an animate or inanimate surface to which energy from the device may be transferred. The term "treat," "treatment" and like terms refer to affecting a target surface with radiant energy emitted from the present device. The term "skin" refers to one or more of the epidermis layer, dermis layer and subcutaneous tissue layer of animals, particularly mammals, including, but not necessarily limited to human beings. The term "tissue" refers to animal living tissue including skin.

In one aspect, the application provides an energy emission device operationally configured to inhibit an individual such as a healthcare provider from issuing an unintended energy dosage that may potentially harm a patient, the healthcare provider, passersby, adjacent equipment and/or other nearby surfaces.

In another aspect, the application provides an energy emission device including a proximity sensor effective to prevent unintended operation of the device.

In another aspect, the application provides an energy emission device including a projected field sensor effective to prevent unintended operation of the device.

In another aspect, the application provides an energy emission device including a projected capacitance sensor effective to prevent unintended operation of the device.

In another aspect, the application provides an energy emission device including an inductive proximity sensor effective to prevent unintended operation of the device.

In another aspect, the application provides an energy emission device including a photoelectric sensor effective to prevent unintended operation of the device.

In another aspect, the application provides an energy emission device including a proximity sensor operationally configured to detect the spatial relationship between the sensor and a surface targeted for energy dosing.

In another aspect, the application provides an energy emission device including a projected field sensor operationally configured to detect the spatial relationship between the sensor and a surface targeted for energy dosing.

In another aspect, the application provides an energy emission device including a projected capacitance sensor operationally configured to detect the spatial relationship between the sensor and a surface targeted for energy dosing.

In another aspect, the application provides an energy emission device including an inductive proximity sensor operationally configured to detect the spatial relationship between the sensor and a surface targeted for energy dosing.

In another aspect, the application provides an energy emission device including a projected capacitance sensor having a void there through, the sensor being oriented about an aperture of the device whereby energy to be emitted out from the device may pass through the sensor prior to passing out through the aperture.

In another aspect, the application provides an energy emission device including a proximity sensor operationally configured to detect the spatial relationship between the sensor and a surface targeted for receiving energy emitted from the device.

In another aspect, the application provides an energy emission device operationally configured to emit energy through an aperture to a target surface. The device further includes a proximity sensor operationally configured to detect the spatial relationship between the target surface and the perimeter of the aperture of the device.

In another aspect, the application provides an energy emission device including a proximity sensor operationally configured to detect a spaced apart target surface through a non-electrically conductive medium.

In another aspect, the application provides an energy emission device including a proximity sensor capable of operating to detect a spaced apart target surface while not being in direct electrical connection to the device. As one example, the proximity sensor may be operationally configured to recognize differences in electric potential with regard to a target surface.

In another aspect, the application provides an energy emission device operationally configured to deliver radiant energy to biological tissue.

In another aspect, the application provides an energy emission device for treating an individual with radiant energy. The strength of dose, length of dosage, and frequency of dosage may be predetermined as desired. Likewise, the surface area to be treated may be predetermined as desired.

In another aspect, the application provides a mobile energy emission device operationally configured to emit predetermined dosages of energy to one or more target surfaces of an individual.

In another aspect, the application provides an energy emission device including pre-programmed energy auto-dosage sequences. In one suitable embodiment, the auto-dosage sequence may be at least partially activated by the detection of a target surface via a sensor means of the device.

In another aspect, the application provides an energy emission device having a self-contained energy source for generating radiant energy.

In another aspect, the application provides an energy emission device in communication with a stand alone energy source for generating radiant energy.

In another aspect, the application provides an energy emission device in communication with an energy source via a fiber-optic cable.

In another aspect, the application provides a handheld energy emission device.

In another aspect, the application provides a handheld energy emission device including a pistol type grip.

In another aspect, the application provides a handheld energy emission device including a pistol type grip and trigger mechanism, the device being operationally configured to operate in a manner similar as a pistol type firearm including pointing the device toward a target and pulling the trigger to emit radiant energy toward the target.

In another aspect, the application provides a handheld energy emission device including a two-way trigger means.

In another aspect, the application provides a system including a handheld energy emission device and a power console for providing power to the device, the console being operationally configured to store one or more devices during periods of device non-use. The console may also be operationally configured to recharge one or more devices during periods of device non-use.

In another aspect, the application provides an energy emission device operationally configured to allow a user to choose the type of radiant energy to be used in conjunction with the device.

In another aspect, the application provides an energy emission device including a radiant energy source in close proximity to an aperture for emitting energy out from the device.

In another aspect, the application provides an energy emission device operationally configured to give a device operator thermal management over the device during use.

In another aspect, the application provides an energy emission device operationally configured to avoid or prevent overlapping dosages of energy applied to a target surface.

In another aspect, the application provides an energy emission device having safety mechanisms operationally configured to prevent unintended energy emission during use.

In another aspect, the application provides an ambidextrous, ergonomic, and agile handheld energy emission device.

In another aspect, the application provides an energy emission device including light emitting diode (LED) technology for the treatment of skin disorders or conditions.

In another aspect, the application provides an energy emission device including a means for calibrating a proximity sensor of the device.

In another aspect, the application provides an energy emission device having and audio and/or visual signal to indicate when radiant energy is being emitted from the device and/or to indicate when radiant energy emission is completed.

In another aspect, the application provides a FCC, CE and RoHS approved energy emission device as understood by persons of ordinary skill in the art of electronic devices.

In another aspect, the application provides an energy emission device that may be built to scale.

In another aspect, the application provides an energy emission device including an aperture for release of radiant energy, wherein substantially the entire outer surface of the aperture may be set flush against a target surface during operation.

In another aspect, the application provides an energy emission device including a sensing means operational independent of the outer configuration of the device itself.

In another aspect, the application provides a radiant energy emission device operationally configured to emit energy for treating skin conditions including, but not necessarily limited to psoriasis, eczema, vitiligo, atopic dermatitis, seborrheic dermatitis, acne, and combinations thereof.

DISCUSSION OF THE DEVICE, SYSTEM AND METHOD

To better understand the novelty of the device, system, and method of use thereof, reference is hereafter made to the accompanying drawings. Generally, a device having safety mechanisms used for preventing unintended energy emissions and/or alleviating or minimizing operator strain during use is provided.

With reference now to a simplified illustration of the invention as provided in FIG. 1, an energy emitting device 10 is provided having an outer protective housing 12, an opening or aperture 14 there through, and a sensor means 16 (not shown) within the housing 12 operationally configured to detect the spatial relationship between the sensor means 16 and a separate target surface. Suitably, the housing 12 is operationally configured to contain energy in a manner effective to limit energy emission through only the aperture 14.

In one embodiment, the device 10 may be powered via a common wall outlet. In another embodiment, the device 10 may be powered by a separate power supply. In still another embodiment, the device 10 may be self powered, i.e., battery powered with either or both rechargeable battery means or disposable battery means.

Figure 2:
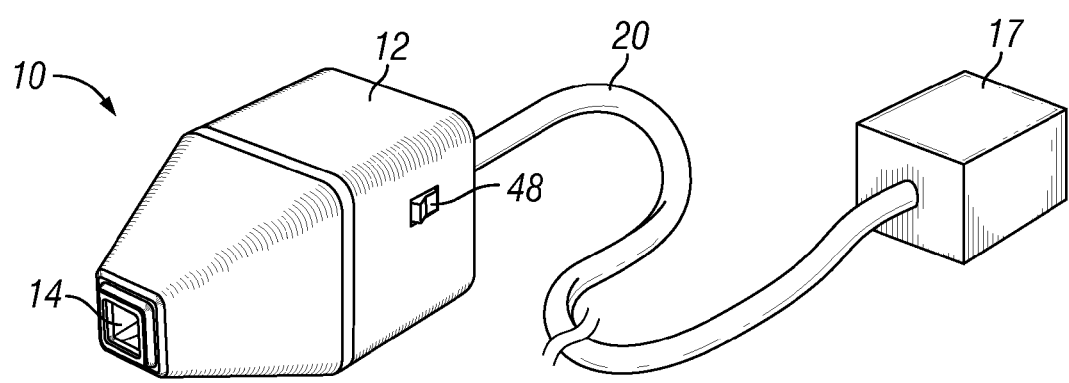
FIG. 2 is a perspective view of an embodiment of the present energy emitting treatment device including an energy conduit and a separate power source and/or energy source.

Suitably, the device 10 is operationally configured to receive radiant energy therein and allow for the emission of radiant energy out through the aperture 14 toward a target surface. As shown in FIG. 2, the radiant energy source may be housed within a component 17 apart from the device 10 whereby the energy source 18 is in radiant communication with the device 10. For example, the device 10 may be in radiant communication with an energy source via a radiant energy conduit 20 or optical tether effective for linking the component 17 to the device 10. It is also contemplated that the component 17 may be operationally configured to provide both electrical power, means for communicating information, and radiant energy to the device 10. In still another embodiment, a device 10 may also be provided having its own radiant energy source 18 within the housing 12 while being powered by a separate power source. In a particularly advantageous embodiment, the device 10 may be provided with a radiant energy source 18 fitted within the housing 12 effective for the device 10 to be handheld during use, eliminating the need for a separate energy source 18 and optical tether 20. Suitable radiant energy conduits include, but are not necessarily limited to fiber-optic conduit, fluid-filled conduit, light pipe, antennas, and prisms.

Figure 3:
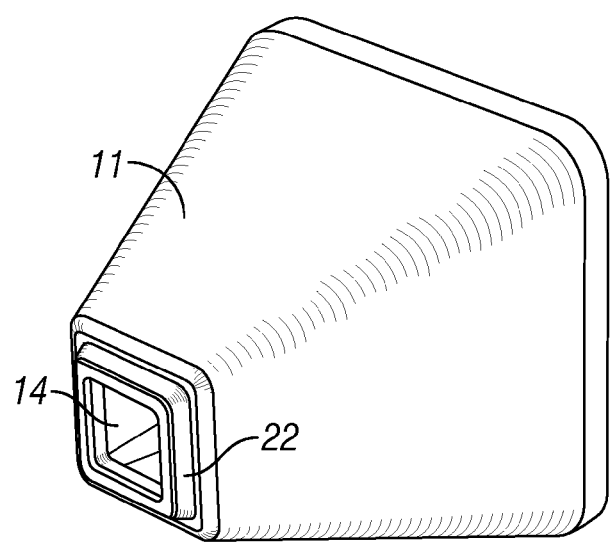
FIG. 3 is a perspective view of a nose portion of the embodiment of the device of FIG. 1.

With reference to FIG. 3, the aperture 14 is suitably operationally configured to allow for the passage of radiant energy there through while simultaneously providing a seal for the housing 12 against external influences such as the intrusion of liquids, dirt, dust, and other solid objects that may affect the working components of the device 10. For the purpose of this application, the term "aperture" refers to the surface along the device 10 where radiant energy exits the device 10. For purposes of this application, where the energy source 18 is configured to emit radiant energy, the aperture 14 suitably includes a physical barrier 15 (see FIG. 4) separating the energy source 18 within the housing 12 from the ambient environment outside the device 10. A suitable aperture barrier 15 is sufficiently transparent to radiant energy. Although not limited to a particular material of construction, suitable aperture barriers 15 are constructed from materials including, but not necessarily limited to sapphire, quartz, glass, polymeric material, metallic surfaces, and combinations thereof. Preferably, the aperture barrier 15 is constructed from a medium that provides the best combination of transmissivity and durability for a particular electromagnetic radiation. In one particularly advantageous embodiment of a device 10 provided with an UV energy source 18, the aperture barrier 15 includes an optical window constructed from sapphire. In another particularly advantageous embodiment of a device 10 provided with an UV energy source 18, the aperture barrier 15 includes an optical window constructed from UV grade fused silica. For referencing purposes, the aperture 14 may be considered as being located on a front side of the device 10. Thus, in operation the aperture 14 suitably faces a target surface while the operator of the device 10 is suitably positioned opposite the aperture 14 toward the back side of the device 10.

In the particular embodiment of FIG. 3, the aperture 14 is disposed along a portion of the housing 12 herein referred to as a nose 11, the nose 11 including an inner surface configuration effective to focus emitted energy toward the aperture 14. In addition, the aperture barrier 15 may be operationally configured to focus energy out from the device 10. In still another embodiment, the device 10 may include a conduit for directing energy from the energy source 18 to the aperture 14. Thus, the inner surface configuration of the housing 12 (the nose 11 portion of FIG. 3), the aperture barrier 15, and conduit materials may be used in any combination to yield energy of particular output intensity from the device 10.

As shown, the device 10 may further comprise a bezel 22 for providing a perimeter border for the aperture 14. In one embodiment, the bezel 22 may be operationally configured to detect the presence of a target surface in front of the aperture 14. In an embodiment of operation where the aperture 14 of the device 10 is to be placed into contact with a target surface, e.g., a patient's skin for administration of dosage of therapeutic energy, the bezel 22 is suitably the first part of the device 10 to contact a target surface. In one suitable embodiment, the bezel 22 may include a resilient means for physical movement or compression of the bezel 22 as the bezel 22 contacts a target surface. In another embodiment, the nose 11 may include a resilient means for physical movement or compression of the nose 11 in relation to the remaining housing 12 as the bezel 22 contacts a target surface.

In another embodiment, the bezel 22 may include one or more pressure sensors where as a target surface is detected either mechanically or electronically energy is suitably transmitted from the bezel 22 to the one or more pressure sensors. As discussed in detail below, once the device 10 detects the presence of a target surface within a predetermined proximity to the device 10, the device 10 is suitably operationally configured to automatically emit radiant energy, or provide for manual radiant energy emission activation. In the absence of a target surface, the device 10 is suitably disabled wherein the device 10 is not able to emit radiant energy.

In another embodiment, the bezel 22 may be utilized to make a temporary indention on a target surface effective to provide a device 10 operator with a means for identifying a prior treatment locale along the target surface. Once a dose is applied to the target surface, an operator may effectively apply further doses to surface areas other than prior treatment locales. In still another embodiment, the bezel 22 may be operationally configured to provide a seal along the perimeter of a target surface area effectively containing radiant energy therein during use.

Figure 4:
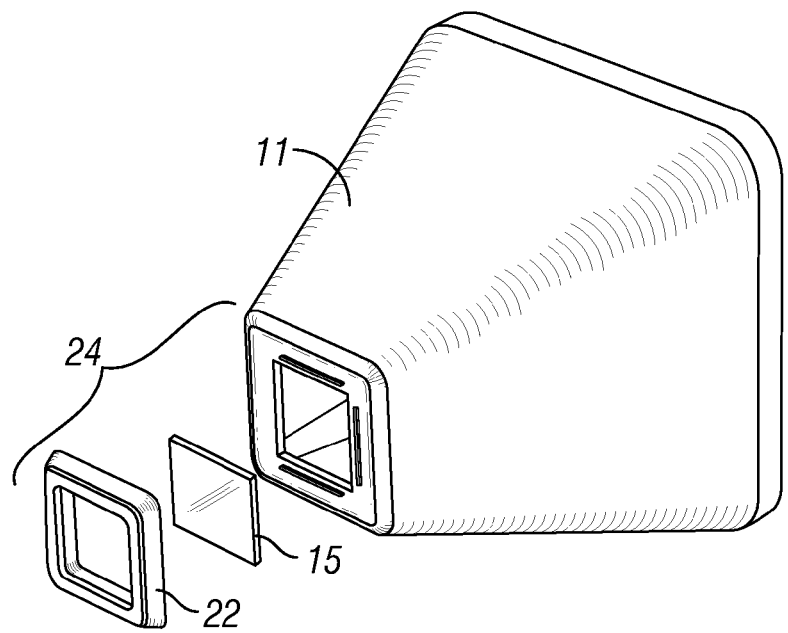
FIG. 4 is a perspective exploded view of the nose portion of FIG. 3 illustrating an aperture barrier and bezel attachable to the nose portion.

Although not limited to a particular configuration, one suitable aperture 14 and bezel 22 thereof may include an aperture assembly 24 as illustrated in FIG. 4. In addition to having the ability to detect a target surface either mechanically or electronically during operation of the device 10, the bezel 22 of the aperture assembly 24 may be (1) releasably attachable to the housing 12, and (2) operationally configured to maintain the aperture barrier 15 in a sealed position across the aperture 14 during operation of the device 10. The aperture assembly 24 may be attached to the nose 11 via threaded fasteners such as screws. In another embodiment, the aperture assembly 24 may be configured to screw or snap directly into the nose 11 of the device 10. As desired, one or more seals may be incorporated into the aperture assembly 24 to ensure that the aperture 14 is sealed during operation of the device 10. Suitable seals include, but are not necessarily limited to o-rings and gasket materials. In still another embodiment, the aperture assembly 24 may be provided as a permanent fixture of the device 10.

Although not limited to a particular material of construction, the bezel 22 is suitably constructed from a like material as the housing 12. As such, the various components of the device 10 are suitably constructed from one or more materials including but not necessarily limited to those materials resistant to chipping, cracking, excessive bending and reshaping as a result of ozone, ultra-violet radiation, weathering, heat, moisture, other outside mechanical and chemical influences, as well as various impacts and other loads placed on the device 10. Suitable materials of construction include, but are not necessarily limited to metals, polymeric materials including polymeric UV-stabilized polymeric materials, rubbers, woods, fiberglass, filled composite materials, and combinations thereof. In a particularly advantageous embodiment of the device 10 for treating human tissue with radiant energy, the housing 12, nose 11, and bezel 22 are suitably constructed from a molded plastic and the aperture barrier 15 is suitably constructed from fused silica.

Figure 5:
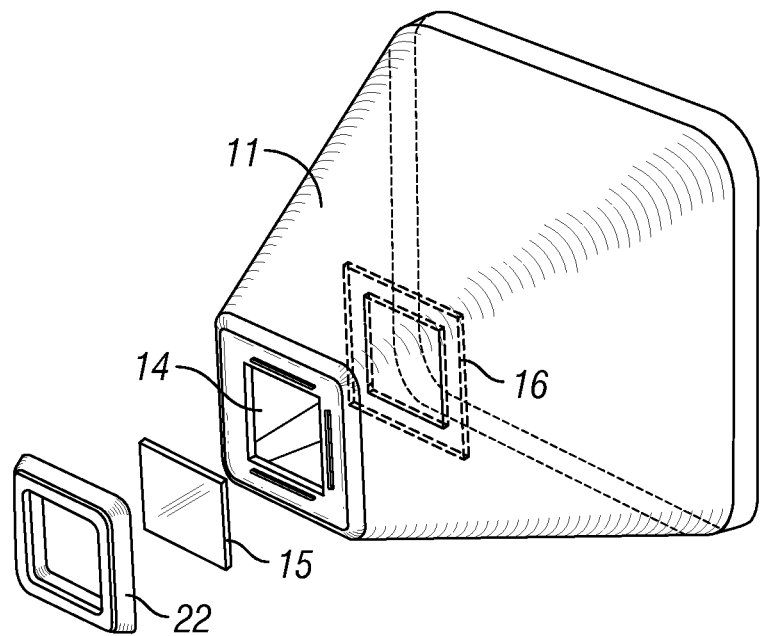
FIG. 5 is a perspective phantom type view of the nose portion of FIG. 3 illustrating a sensor means housed within the nose portion.

Turning to FIG. 5, a sensor means 16 is suitably situated within the housing 12 in a manner effective for the sensor means 16 to detect the spatial relationship between the sensor means 16 and a target surface or between the aperture 14 and the target surface as desired. In other words, a suitable sensor means 16 is operationally configured to detect a target surface through a medium including, but not necessarily limited to a non-electrically conductive medium. A suitable sensor means 16 includes a projected field sensor or proximity sensor operationally configured to detect the presence of nearby objects without any physical or direct electrical contact between the device 10 and a target surface.

Depending on the intended use of the device 10, the device 10 may be fitted with a sensor means 16 operationally configured to detect one or more predetermined target surfaces. In one suitable embodiment for use in connection with conductive target surfaces or surfaces having dielectric properties, the device 10 may employ projected capacitance sensor technology. Suitable projected capacitance sensor technology includes, but is not necessarily limited to human interface device technology that measures changes in an electric field as understood by persons of ordinary skill in the art of sensors. Suitably, projected capacitance sensors 16 may be operationally configured to detect the spatial relationship between the sensor 16 and a target surface from a predetermined distance from the target surface up to actual contact of the device 10 depending on the type of sensor 16 employed, the location of the sensor 16 within the device 10, and the shape and size of the device 10.

In another embodiment it is contemplated that an inductive proximity sensor means may be employed for non-contact detection of metal containing target surfaces. As understood by persons of ordinary skill in the art of sensors, as a metal target surface enters a sensing field, eddy currents are induced in the target surface reducing the signal amplitude and triggering a change of state at the sensor output. Such technology may be employed as desired.

In another embodiment, a touch detection sensor means may be employed as desired. Suitable touch detection technology includes, but is not necessarily limited to resistive sensor technology, surface acoustic wave sensor technology, capacitive sensor technology, projected capacitance, strain gauge technology, optical imaging, dispersive signal technology, and acoustic pulse recognition.

In terms of a device 10 for targeting human skin with radiant energy, a suitable sensor means 16 includes, but is not necessarily limited to a projected capacitive touch sensor or a capacitive proximity sensor 16. As understood by persons of ordinary skill in the art of sensors, capacitive proximity sensing or capacitive touch sensing involves the detection of change in the electric field between two or more bodies. These bodies are typically conductive, and the medium between the bodies is some form of dielectric, e.g., air or skin. By applying a voltage between the conductive bodies, an electric field is setup between them. Assuming the surface area of the two conductive bodies does not change, and the material between the conductive bodies does not change, then altering the distance between them can be correlated to changes registered in the electric field. To explain further, where all other variables are held constant, if two conductive bodies are brought closer together the electric field will increase in intensity, and vice versa. In typical capacitance touch sensing, one of the conducting bodies is part of the sensor itself. The other body is the external object or surface to be detected, the external object capable of carrying an electric charge. In the case of a human body, the body's internal fluids are electrolytic, and the skin is a dielectric. As the body, e.g., human skin and underlying electrolytic fluids, draws near to, but not necessarily into contact with a sensor 16, the sensor 16 in the device 10 suitably registers a change in the electric field. It is the recognition of the change in electric field that herein determines the activation ability of the device 10 with regard to its ability to emit radiant energy out through the aperture 14.

With attention to FIG. 5, a simplified embodiment of a projected capacitive sensor 16 suitable for use with skin is shown. As understood by persons of ordinary skill in the art of sensors, a suitable sensor 16 used herein is effective to sense a change in the field between the sensor 16 and the target surface as described previously. In this embodiment, one or more sensors 16 may be disposed about the perimeter of the aperture 14 in a manner effective to allow radiant energy to pass through the sensor 16 on route toward the aperture 14 and a target surface out beyond the aperture 14 of the device 10. By locating sensor(s) 16 near the aperture 14, the device 10 is operationally configured to detect the target skin without the device 10 necessarily having to contact the skin, thereby providing for non-contact sensing of the target skin surface. Moreover, an open center sensor 16, i.e., a sensor 16 having a void there through, as shown in FIG. 5, is suitably operationally configured to substantially contour along the perimeter of the aperture 14 in a manner effective for the sensor 16 to register change in electric field along the entire perimeter of the aperture 14. Additionally, an open center sensor 16, alone or in addition to a highly transmissive aperture 14, suitably allows for unimpeded flow of radiant energy through the sensor 16 toward the aperture 14 providing for reduction or elimination of attenuation of the radiant energy emission during device 10 operation.

In addition, the sensor 16 configuration of FIG. 5 eliminates the need for direct electrical connection to the device 10, when used in conjunction with a nose 11 constructed from non-conductive materials. To detail an advantage of the current sensor means 16, if a sensor system were provided as a set of metal prongs as known in the art, and such sensing system was resistive such that the prongs were connected to a circuit and a voltage applied between the prongs, then once both prongs contacted a patient's skin simultaneously, a circuit connected to the prongs may sense a drop in the voltage applied between the prongs as the current from one prong passes electrically through a patient's skin. If a large enough electrical shock happened to pass through a patient from external means while the patient's skin was in contact with the prongs, the electrical shock could travel into the device 10 potentially damaging the device 10. If a large enough electrical shock passed into the device 10 from external means (or was generated internally, e.g., a malfunctioning battery) the shock could possibly pass directly into a patient potentially harming the patient. The sensor means 16 of the present application and the embodiments described herein avoid these prong related concerns of electrical shock because an electrical shock traveling either (1) from a patient to the sensor means 16, or (2) the sensor means 16 to a patient does not have a conductive path, and is thus insufficiently powerful to bridge a non-conductive gap via dielectric breakdown between the device 10 and target patient.

In a particularly advantageous embodiment, the sensor 16 is provided as a printed circuit board ("PCB") with a conductive layer and required electronics, the sensor being located within the nose 11 adjacent the aperture assembly 24. The conductive layer may be constructed from known conductive metals including, but not necessary limited to copper, gold, platinum, silver, and combinations thereof.

When targeting a surface that may have many contours, the present sensor 16 is operationally configured to sense the target skin at any point or several points about the perimeter of the aperture 14. By providing sensing ability about the entire aperture 14 perimeter, the sensor 16 is suitably tuned so that the device 10 may draw substantially near to a target surface without necessarily contacting the surface regardless of the surface contour.

To optimally register change in electric field along the entire aperture 14, the sensor 16 of the printed circuit board is suitably configured to include a cutout or void through its center, the cutout being substantially similar in size and shape as the aperture 14 so that the sensing means of the circuit board lies along the perimeter of the aperture 14 (see FIG. 5). Here, the target surface to be treated with the device 10 may suitably be detected along the entire periphery of the aperture 14 in a manner effective for radiant energy emitted out through the aperture 14 to radiate only the target surface area. Thus, the present sensor means 16 is suitably effective to provide the device 10 with a safety feature for guarding against undesired activation of the device until the aperture 14 of the device 10 lies within a predetermined proximity to a target surface, which in effect also protects against exposing non-target surfaces to the radiant energy projected out through the aperture 14. As discussed below, the present sensor means 16 may also be effective for use in conjunction with a device 10 operationally configured to emit automatic sequences of radiant energy.

Figure 6:
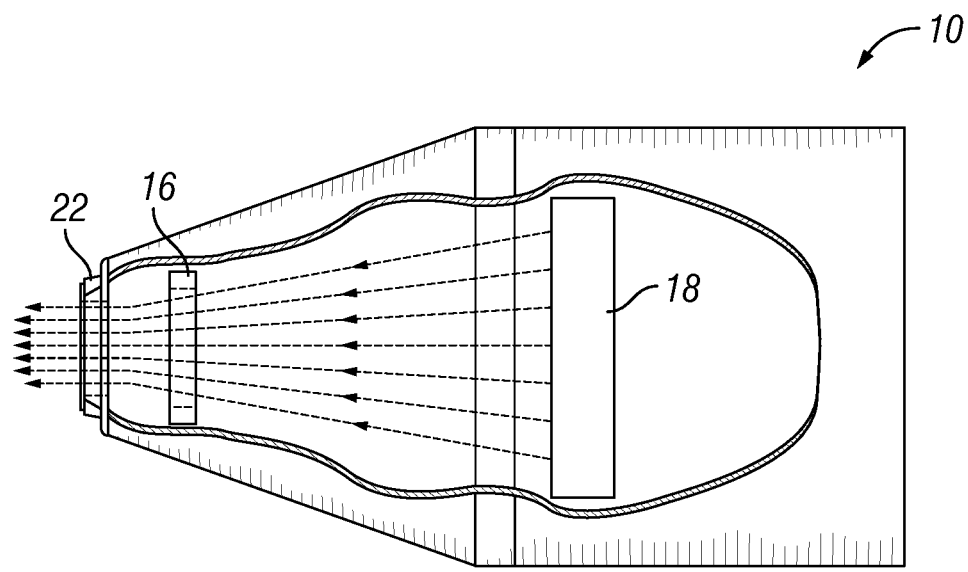
FIG. 6 is a cross-sectional side view of the device of FIG. 1 illustrating exemplary radiant energy directional emission from an internal energy source out through an aperture of the device.

With reference to FIG. 6, a simplified illustration of the device 10 is provided including a radiant energy source 18 configured within the housing 12, the device 10 being operationally configured to project the radiant energy onto a target surface. As shown by the directional arrows in FIG. 6, energy emitted from the energy source 18 is suitably projected in the form of electromagnetic waves through the sensor means 16 past the aperture 14 along a vector toward a target surface. As desired, the energy source 18 of the device 10 may include one or more frequencies of electromagnetic radiation, such as radio waves, microwaves, infrared, near infrared, visible light, ultraviolet light ("UV"), X-rays, gamma rays, high energy gamma rays, and combinations thereof.

Although various frequencies may be used to treat known skin conditions, the following description will discuss treating psoriasis using UV light, a type of treatment hereafter referred to as "targeted UV phototherapy." UV light is electromagnetic radiation having a wavelength shorter than that of visible light but longer than X-rays in the range from about 10 nm to about 400 nm, with energies from about 3 eV to about 124 eV. The three main types of UV light discussed herein include (1) UVA having wavelengths in the range from about 400 nm to about 320 nm; (2) UVB having wavelengths in the range from about 320 nm to about 280 nm; and (3) UVC having wavelengths in the range from about 280 nm to about 100 nm. For treating psoriasis, die-level LEDs are suitably provided for emitting wavelengths from about 395 nm to about 300 nm.

Psoriasis is a skin condition that causes skin redness and irritation. Psoriasis can affect the skin, fingers, toe nails, joints (psoriatic arthritis), and has been linked with generally poorer immune responses to other illnesses and slower recovery times. While there are several forms of a psoriatic outbreak, the most common type is psoriasis vulgaris, also known as plaque psoriasis. Plaque psoriasis is evidenced by patches of skin which may appear red and inflamed and possibly covered by silvery white scaly skin. These areas are typically described as being sore and itchy. Other forms of psoriasis may appear as spots or other shapes and may contain pustules, structures that ooze pus.

To date, various forms of UV light have been implemented in an attempt to treat psoriasis. UV phototherapy treatments typically focus on administration of sub-erythemic dosages ("SEDs") and multiples of a minimum erythemic dose ("MED"). The MED is unique for each patient and refers to the minimum irradiance necessary to cause visible reddening of skin after a certain period of time of exposure to radiation, e.g., UV light. Known devices that administer SED level UV dosages are referred to as "non-targeted UV phototherapy" devices, because these devices often administer UV light to a patient's entire body or large surface areas unnecessarily affecting healthy skin or non-target skin along with the target skin surface area to be treated, and thus cannot deliver greater than a patient's MED without burning or otherwise affecting healthy and/or non-target skin. Conversely, targeted UV phototherapy devices administer more intense UV light, at multiples of a patient's MED, and generally to small body surfaces treating substantially only the target skin surface sparing healthy and/or non-target skin.

To date, UV light sources used to treat psoriatic lesions have included direct sunlight, and conventional illuminators such as UV light bulbs and UV fluorescent lamps, as well as UV-generating gas arc lamps, excimer lasers, and excimer light sources. However, it is difficult to limit sun exposure to only the target surface area of the skin. Also, with regard to targeted UV phototherapy, i.e. administering multiples of a patient's MED per dose, arc lamps and lasers have several drawbacks. For example, in addition to having low life spans, typically about 300 hours or less, the high intensity light output from arc lamps requires optical filtering to potentially eliminate UVC emissions and reduce UVB emissions below about 300 nm. The high intensity UV light from excimer laser sources is monochromatic and within a suitable therapeutic wavelength range, but is more costly than arc lamps and typically requires greater maintenance. To overcome these types of issues, the present device 10 employs one or more Light Emitting Diodes ("LEDs") fabricated in a manner effective to provide (1) substantially even exposure of a target surface of skin with UV light, (2) long energy source life, and suitably (3) limited maintenance.

Figure 7:
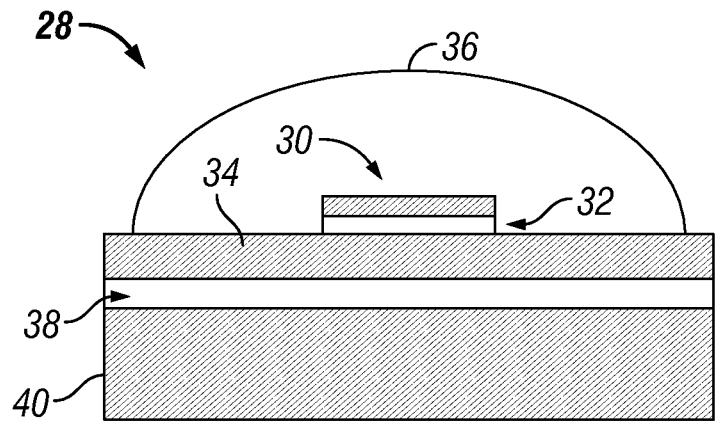
FIG. 7 is a side elevational view of an exemplary LED assembly.

With reference to FIG. 7, a suitable LED assembly 28 includes die-level LED technology as understood by persons of ordinary skill in the art of LEDs. As shown, the LED die 30 is suitably mounted to a sub-mount 32, wherein the sub-mount has conductive traces and conductive surfaces through which an LED die 30 cathode and anode may be connected. The sub-mount 32 is suitably mounted to a first surface of a substrate 34 such as a circuit board wherein wires or other electrical connections are bonded between the electrical paths of the substrate and the conductive surfaces of the sub-mount 32. The LED die 30, sub-mount 32, and a portion of the substrate 34 are suitably housed within an enclosure operationally configured to (1) preserve the LED assembly 28, and in certain instances (2) provide a lens for beneficial optical dispersion of light. As LEDs radiate energy as heat, some form of thermal interface material 38 operationally configured to transfer heat between two surfaces is appositely applied to a second surface of the substrate 34. In one particular embodiment, a heat sink 40 or other form of heat dissipating device may be applied to the free surface of the thermal interface material 38.

LEDs provide a UV light source that is lightweight, small in size, durable, and with an emission spectra approximating a known monochromatic laser profile. UV LED technology affords a light emission spectra that does not typically require optical filtering of undesired wavelengths. Die-level LED assemblies 28 are suitably utilized for smaller, lower profile designs suitable for use with a handheld type device 10 of this application. Appositely, die-level LED assemblies 28 may be mounted directly to a printed circuit board in a larger number per unit area than other known illuminators.

Although not limited to a particular configuration, desired LEDs are suitably arranged in a pattern over a surface area to emit light from the LEDs toward a target surface. As of the date of this application, LED die 30 are commercially provided in a range of about 395 nm to about 300 nm and typically emit about 50 mW/cm$^2$ or less.

Depending on the severity of the psoriasis and the surface area of the target lesion, a suitable device 10 may be operationally configured to provide an array of at least several hundred LED die 30 with near to about 310 nm peak wavelength effective for emitting approximately at least hundreds of mW/cm$^2$ intensity over several seconds. For exemplary purposes only, if a surface area of the target lesion is about 4 cm$^2$, then a typical intensity from about 50 to about 250 mW/cm$^2$, and in some instances even 1.0 W/cm$^2$ or more may be required to treat a psoriatic lesion. As LED technology progresses, less LED die may be required to achieve current optical output intensities. It is also contemplated that LEDs of this application may be further capable of emitting white-light or any portion thereof, e.g., blue-light, as desired.

Figure 8:
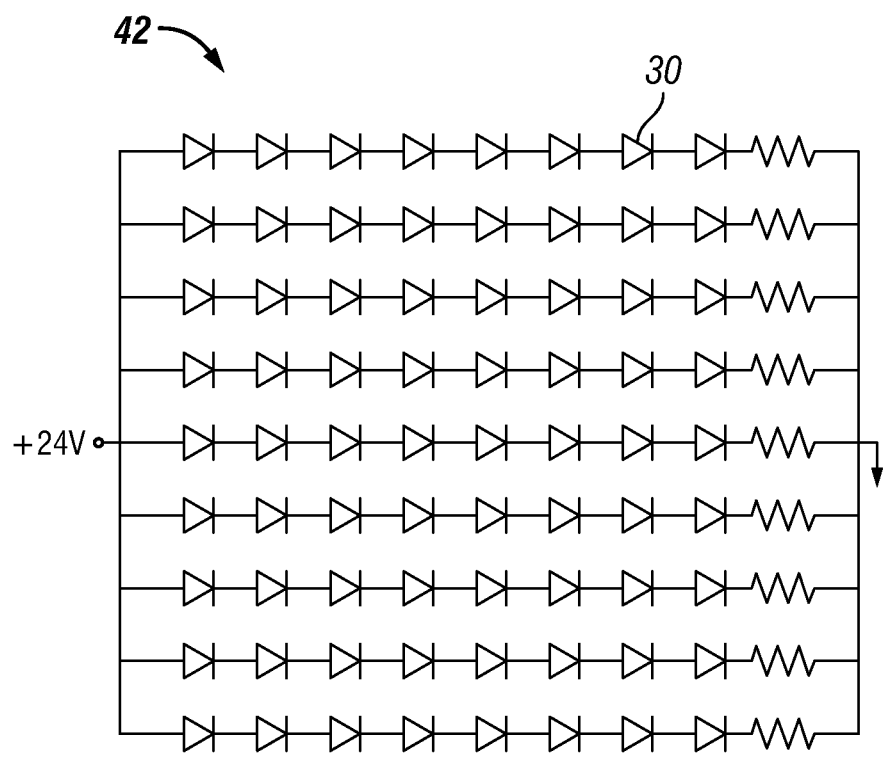
FIG. 8 illustrates an exemplary LED array of the present device.

For desirable treatment applications, a suitable device 10 may include an array of 310 nm LEDs consisting of ten substantially parallel rows, each row containing twenty LED die, the array emitting at least about 50 mW/cm$^2$ of light intensity. Although multiple LED arrangements are contemplated for use herein, one suitable LED array 42 to be employed with the present device 10 is depicted in FIG. 8. In this embodiment, the LED array 42 includes a plurality of light emitting diode banks connected in parallel with the light emitting diodes of each bank being serially connected. By employing a large number of LEDs, a relatively high power light radiation source may be provided. As shown, the LED die 30 (represented by triangles in FIG. 8) are aligned in nine rows of LED die 30, each row containing eight LED die for a total of seventy-two LED die.

Figure 9:
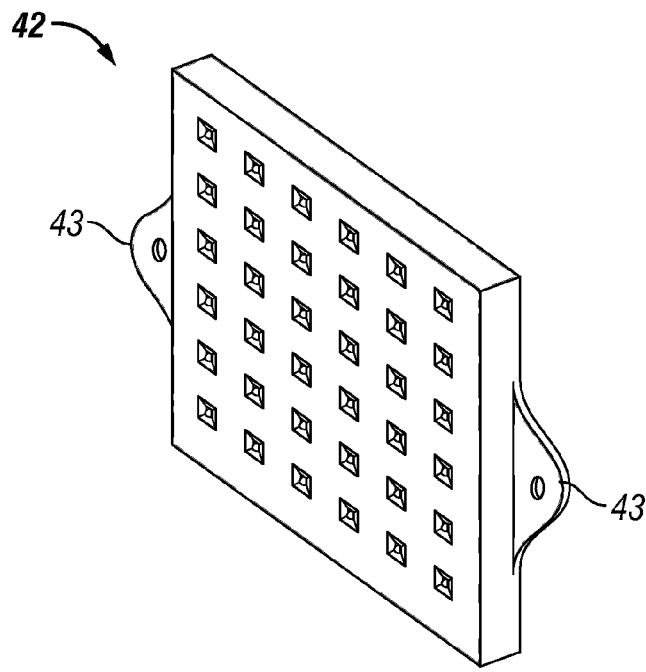
FIG. 9 illustrates an exemplary LED array of the present device including a mounting means for securing the LED array to an internal surface(s) of the device.

With reference to FIG. 9, an LED array 42 of the device 10 may be provided for achieving an electronic circuit of the type represented in FIG. 8, which is (1) effective to provide mounting, (2) designed to focus or collimate optical output or to be oriented to most favorably interact with other focusing structures, and (3) designed to protect the electronics therein. As desired and depending on the inner housing 12 configuration, the LED array 42 may include a mounting means for securing the array 42 to the housing 12 or structures therein. As shown, the array 42 includes two mounting flanges 43 for accepting fasteners there through. Suitable fasteners include mounting screws, mounting posts, and the like. Although the device 10 may be built to scale, a suitable LED array 42 for a handheld device 10 may range from a few millimeters up to several centimeters in length and width. In a particularly advantageous embodiment of the device 10, the LED array 42 includes length and width dimensions substantially similar to or less than the dimensions of the target surface area to be treated using the device 10.

As desired, the present LED array 42 may also include various thermal management characteristics. For example, an array 42 may be arranged wherein each LED die 30 is fixed to a substrate 34 within a cavity or like structure via one or more heat spreading materials to reduce thermal resistance wherein the design of the substrate 34 also works to transfer heat away from the LED during use. Here, suitable heat spreading materials include, but are not necessarily limited to silicon, ceramic materials, sapphire, metals with high thermal conductivity, and combinations thereof.

Other thermal management characteristics may include (1) providing LED arrays 42 utilizing (a) thermally conductive adhesives when and where adhesives are required, and (b) metal core printed circuit boards ("MCPCB") to act as improved heat spreaders; (2) attaching LED arrays 42 to an MCPCB via small mounting screws to ensure good thermal transfer; (3) providing LED arrays 42 making use of high thermal conductivity material heat sinks 40 with large surface areas and mounting such heat sinks 40 with mounting screws as opposed to an adhesive; (4) providing LED arrays 42 utilizing thermoelectric cooling devices; (5) incorporating small fans into the device 10 to extract heat away from the LED array 42; (6) locating all powered LED driving circuitry apart from the LED dies 30, as circuitry may generate heat that may otherwise contribute to heat generated by the LED array 42; (7) utilizing liquid-cooled heat sinks 40 to transfer heat away from the substrate 34, and (8) routing air flow through the device 10 such that cool air may be directed across any hot surfaces of the LED array 42 and thereafter directed away from the LED array 42.

As previously stated, activation of the energy source 18 may be controlled directly by a power source. In particular, the device 10 may include a power switch in communication with the energy source 18, whereby the energy source 18 may be powered by (1) a separate power source located in a separate component 17 as depicted in FIG. 2, (2) plugging the device 10 directly into a wall outlet via a power cord, or (3) the device may be self powered, i.e., battery powered. In one mode of operation, the device 10 may be wholly automated. In another mode of operation, a power switch may be provided to allow for manual operation of the device 10. A suitable power switch includes electrical connections such as wires (not shown) providing electrical communication between the energy source 18, e.g., an LED array 42, and a power source. In such implementation, a switchable power source may selectively provide either a continuous or pulsed operation of the diode banks. In one continuous mode of operation, a selector switch may be used to interconnect a power supply to LED die 30 (shown in FIG. 8 as 12+V). In pulsed operation, small bursts of electrical power may be delivered to the LED array 42 at various frequencies and for various durations, potentially in an attempt to increase LED lifespan and reduce energy consumption. Although not limited to any one mode of operation, suitable manual power switches include, but are not necessarily limited to bush-button switches, toggle switches, rocker switches, slide switches, and foot pedals. Although the placement of the power switch may vary, a suitable power switch is located in convenient proximity to the operator of the device 10.

Figure 10:
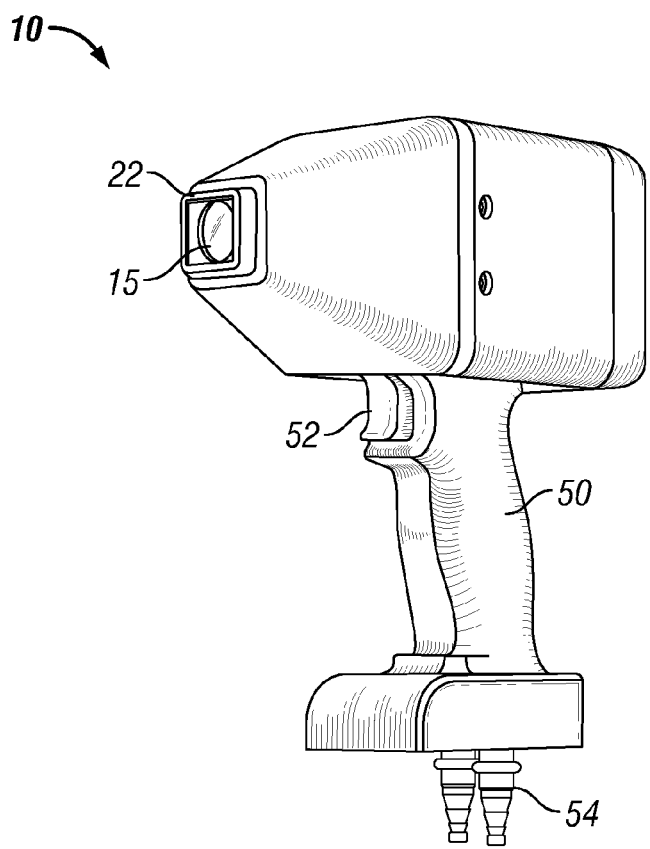
FIG. 10 is a side perspective view of another embodiment of the device including a pistol type grip and trigger.

In one suitable embodiment, activation of the energy source 18 may be controlled by a separate energy activation switch 48 as shown in FIG. 2. In a particularly advantageous embodiment of the device 10 as shown in FIG. 10, the device 10 suitably has a pistol type grip 50 including an energy activation switch in the form of a two-way trigger 52 providing for hand held operation of the device 10 and finger activation of the energy source 18 via trigger 52. In operation, once the sensor 16 detects a target surface, another electrical sensor in an electronic device controller of the device 10, and in communication with the sensor 16, may receive a signal from the sensor 16 allowing for activation of the energy activation switch (trigger 52) allowing for radiant energy activation from the energy source 18. Suitably, electrical communication of the device may be accomplished using solid state electronics or custom electronics designs as understood by persons of ordinary skill in the art of electronics.

Similar as the power source, energy activation switches 48 may include, but are not necessarily limited to bush-button switches, toggle switches, rocker switches, slide switches, and foot pedals. In addition, the device 10 shown in FIG. 10 is suitably operationally configured for ambidextrous use in both substantially vertical and substantially horizontal positions of the device 10. It is also contemplated that the device 10 of FIG. 10 may be fitted with a bulb or like indicator to inform a user as to when the device 10 is in position or otherwise set to emit radiant energy.

As further shown in FIG. 10, in an embodiment where the energy source 18 is housed separate from the device 10, the device 10 may include one or more connectors 54 for releasable or permanent attachment of the device 10 to a radiant energy conduit 20. In a battery powered embodiment of the device 10 of FIG. 10, one or more connectors 54 may be included for recharging and/or facilitating electronic communications for the device 10. Thus, the device 10 may be provided with a separate docking station for recharging purposes, or the device 10 may be provided with charging cables, such as USB charging cables, or other custom wire harnesses as desired. As technology advantages, other means may be provided for recharging purposes, including for example, wireless energy transfer.

OPERATION OF THE DEVICE

Figure 16:
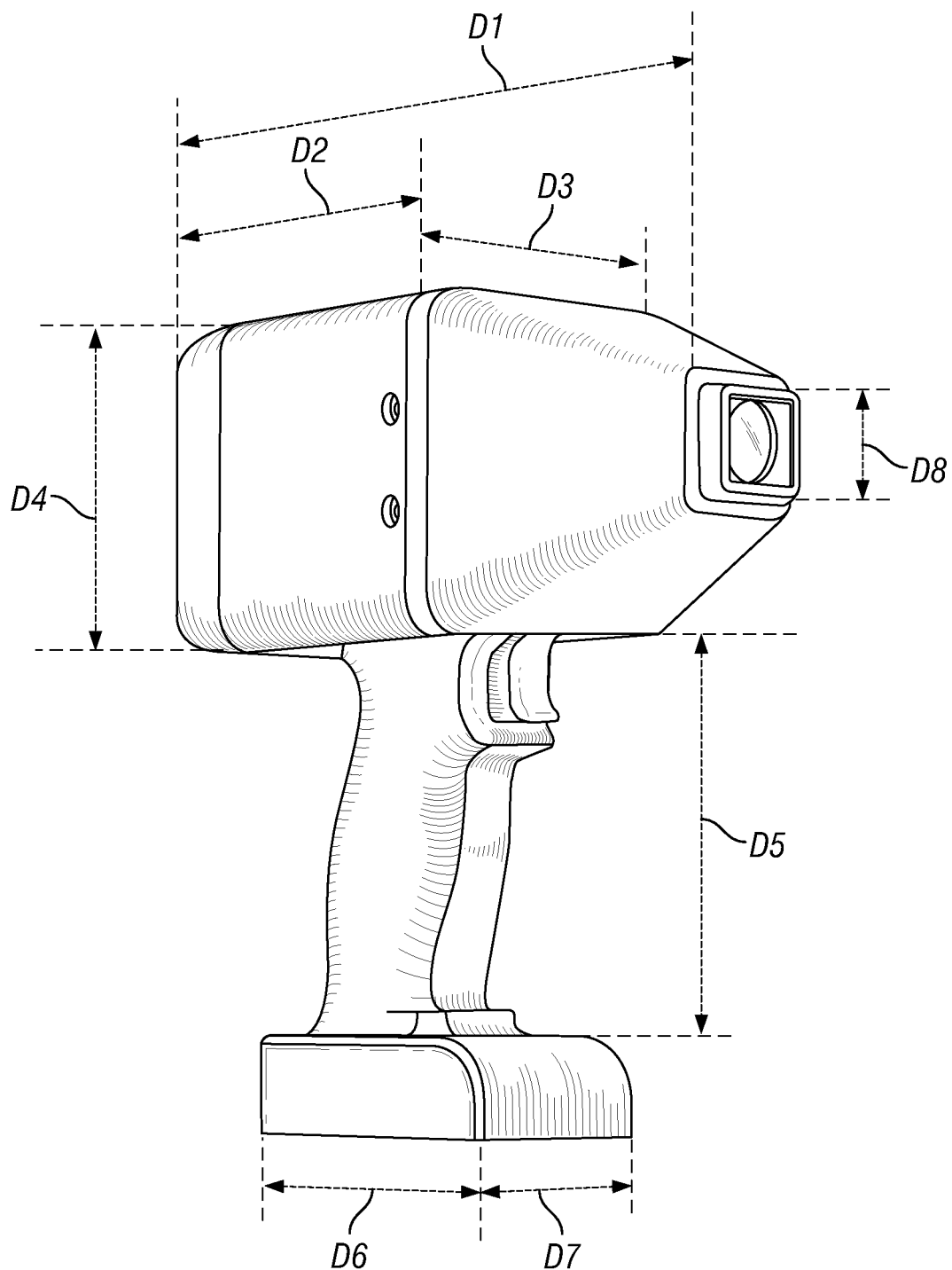
FIG. 16 is another perspective view of an embodiment of the device.
Figure 17:
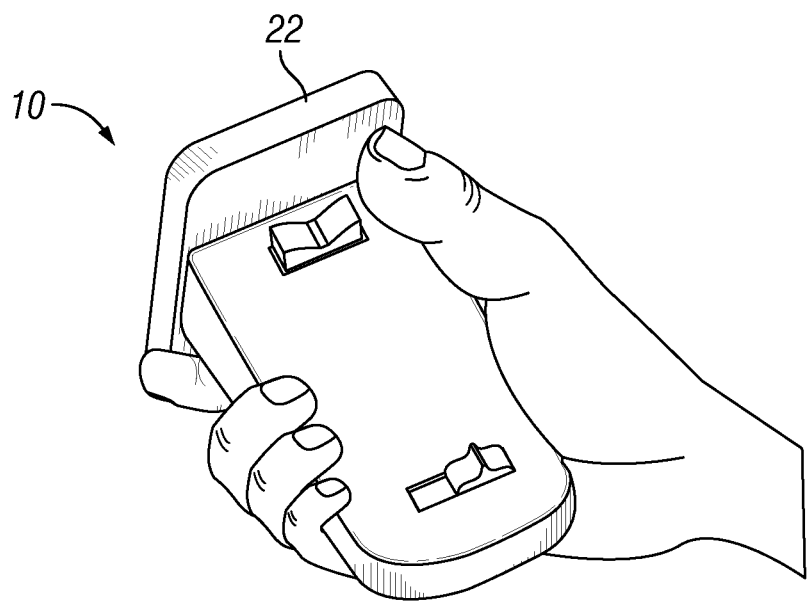
FIG. 17 illustrates another embodiment of the device.
Figure 18:
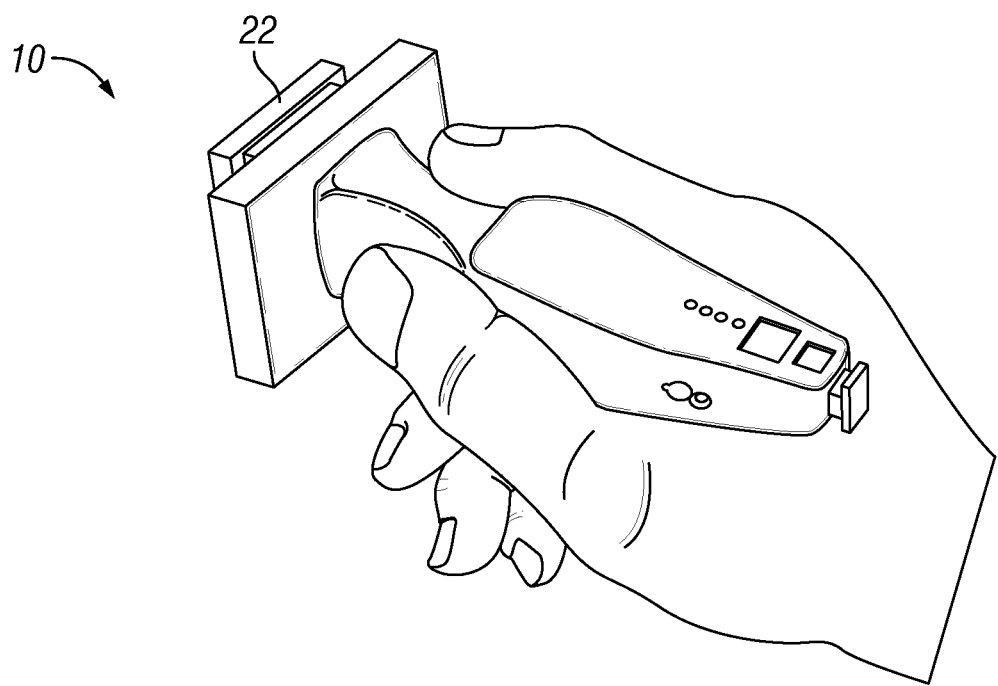
FIG. 18 illustrates another embodiment of the device.

For purposes of operation explanation, the device of FIG. 16 is discussed in terms of treating psoriasis. Although the device 10 may be used in many environments and by any individual, for simplicity, the present operation is discussed in terms of medicinal treatment of psoriasis as performed by a healthcare provider.

Figure 11:
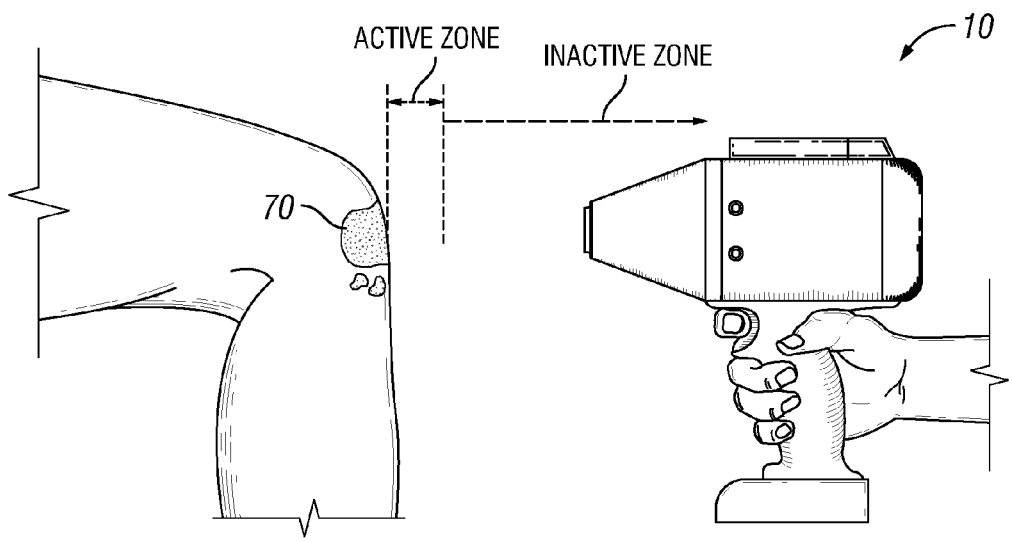
FIG. 11 illustrates operation of the device including targeting a skin lesion of a person's knee, the device being in a non-active mode.
Figure 12:
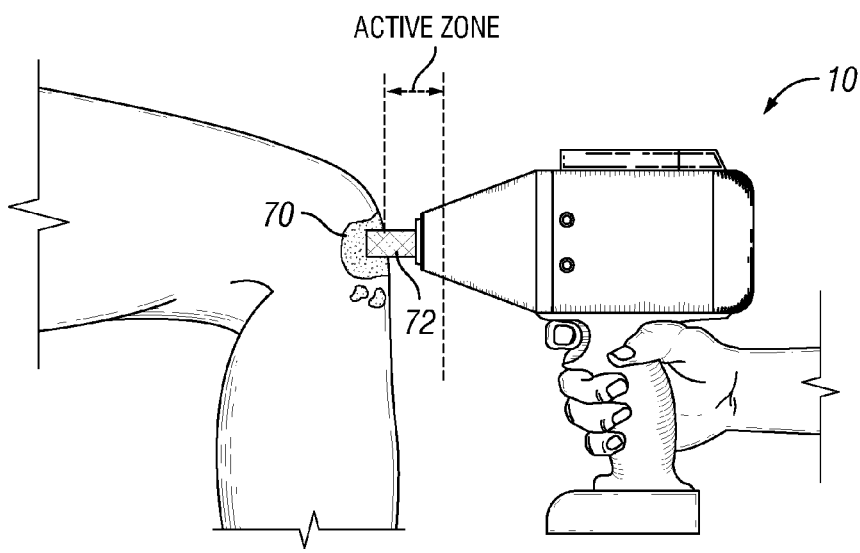
FIG. 12 illustrates operation of the device including targeting a skin lesion of a person's knee, the device being in an active mode for emitting radiant energy to the skin lesion as shown.

Suitably, the target lesion of a patient's skin is exposed in a manner effective to concentrate the device 10 to only the target lesion and not non-target portions of his/her skin. As depicted in FIGS. 11 and 12, which illustrate treatment of a psoriatic lesion 70 along the knee of a patient, the patient may suitably bend the knee to form an apex type target skin surface of the lesion 70 to assist the healthcare provider in focusing the device 10 on the target lesion 70.

In operation, once a patient is situated and the target lesion 70 exposed, a powered device 10 may be directed toward the target lesion 70 as shown in FIG. 11. As explained above, if the sensor means 16 is too far from the target lesion 70, then the sensor means 16 provides an open circuit disabling any manual trigger 52 activation of the LED energy source 18. As the device 10 is directed toward the target lesion 70 the sensor means 16 suitably detects the spatial relationship between the sensor means 16 and the target lesion 70 at a desired or preset distance. Once the sensor means 16 comes within a desired distance to the target lesion 70, the sensor means 16 provides a closed circuit enabling manual trigger 52 activation of the LED energy source 18.

For purposes of targeted UV phototherapy, the device of FIG. 11 is suitably operationally configured to emit UV light 72 out through the aperture 14 once the bezel 22 of the device 10 is within an active zone as shown in FIG. 12 up to direct contact with the target lesion 70. In a particular advantageous embodiment, the active zone of the device 10 is suitably defined as being once the bezel 22 of the device 10 is within about 1.252 cm (about 0.5 inches) or closer to the target lesion 70. Activation of the device 10 without making actual contact with the target lesion 70 may be desirable in an attempt to avoid infection and/or or further irritation of the lesion 70.

In addition, the device 10 may be operationally configured to emit single doses of UV light equal to one UV light dose emission per single trigger 52 activation, i.e., once the trigger 52 is "pulled" as commonly referred to in pistol grip type configurations. For example, a single dose of UV light may include an emission period from about 0.10 seconds to about 20.0 seconds. In another embodiment, the device 10 may be operationally configured to emit prolonged single doses of UV light per single trigger 52 activation, for example, from about 0.1 seconds to about 20.0 seconds. Also, the emission period may be varied as desired. In another embodiment, the device 10 may be operationally configured to emit multiple doses of UV light per single trigger 52 activation in the time ranges listed above. In multiple dosing type operations, the device 10 may be operationally configured to (1) emit doses of UV light in successive time intervals, wherein time intervals between dosing is substantially similar or dissimilar as desired, (2) emit doses of UV light in dissimilar time intervals with time intervals between dosing being substantially similar or dissimilar as desired. Each of the above dosing specifications may be implemented as determined by the type of lesion 70 and as determined by a healthcare provider according to the anticipated treatment logistics. For example, where a single healthcare provider is assigned to provide the treatment to a patient throughout the course of a single day, operator fatigue may set in. Thus, it may be beneficial to make use of a device 10 having preprogrammed auto-dosage sequences. In one exemplary scenario, the device 10 may be programmed to provide a dosage of UV light to a lesion 70 for a period of time, wherein once the dosing is finished, the device 10 remains in a non-dosing state for a period of time before providing a subsequent dosage. The idea here is for the healthcare provider to initiate the first dosage and then to just simply hold the device during subsequent treatment dosings.

In one implementation, the energy dosage intensity of individual doses may be pre-programmed to vary automatically, or an operator may manually adjust the energy dosage intensity prior to trigger 52 activation. In another implementation, the trigger 52 may be held in a compressed state whereby a single prolonged dose may be administered to a target lesion 70, or in the alternative, multiple doses may be administered to a target lesion 70. It is further contemplated that the trigger 52 may be pulled and released to initiate a preprogrammed UV light emission sequence including any combination of parameters including for example (1) total individual energy emission dosages to be administered to a particular patient, (2) energy intensity per individual dosing, and (3) the emission time of individual doses.

Also, larger target lesion 70 surface areas about 250 cm$^2$ or more, darker-pigmented skin types, and severe lesions 70 may require extended periods of exposure time to UV light, e.g., about ten minutes or more. In such scenario, each dose suitably lasts several seconds, and each dose is administered to a small patch of skin, e.g., about 4.0 cm² or less, until the entire target lesion 70 surface area has been treated with UV light.

The invention will be better understood with reference to the following non-limiting examples, which are illustrative only and not intended to limit the present invention to a particular embodiment.

EXAMPLE 1

In a first non-limiting example, a hand held battery powered targeted UV phototherapy device 10 operationally configured to expose UV light at about 4.0 cm² per dose during operation is provided for treating a psoriatic lesion 70 having a surface of about 8.0 cm². The device 10 being programmed for auto-dosing sequences. The device 10 includes:

a total of 20 UVA LEDs at 385 nm+/−10 nm;

a total of 200 UVB LEDs at 310 nm+/−2.5 nm; and an aperture barrier constructed from UV grade fused silica about 0.2032 cm (0.08 inches) thick.

Treatment of an exposed lesion 70 is administered as follows:

(1) a healthcare provider turns the power switch of the device 10 to an ON position;

(2) the healthcare provider programs the device 10 to an auto-dosage sequence setting;

(3) the healthcare provider places the device 10 in front of the target lesion 70 and directs the device 10 toward a first target region of the lesion 70;

(4) once the device 10 draws to within a predetermined distance of the lesion 70, a capacitance sensor 16 within the device 10 registers a change in the electric field about the sensor 16 enabling the trigger 52 to activate UV light emission from an LED array 42 housed within the device 10;

(5) the healthcare provider then initiates UV light emission by pulling the trigger 52 with his/her finger;

(6) the device 10 emits a first pre-programmed dosage of UV light, an audio and/or visual signal is set off from the device 10 to indicate that a UV dosage is being emitted;

(7) once the first dosing has completed, the healthcare provider moves and aims the device 10 to a second target area of the lesion 70;

(8) steps 4, 5, and 6 are repeated;

(9) the power switch is turned to an OFF position and the device 10 is stored away.

EXAMPLE 2

Figure 13:
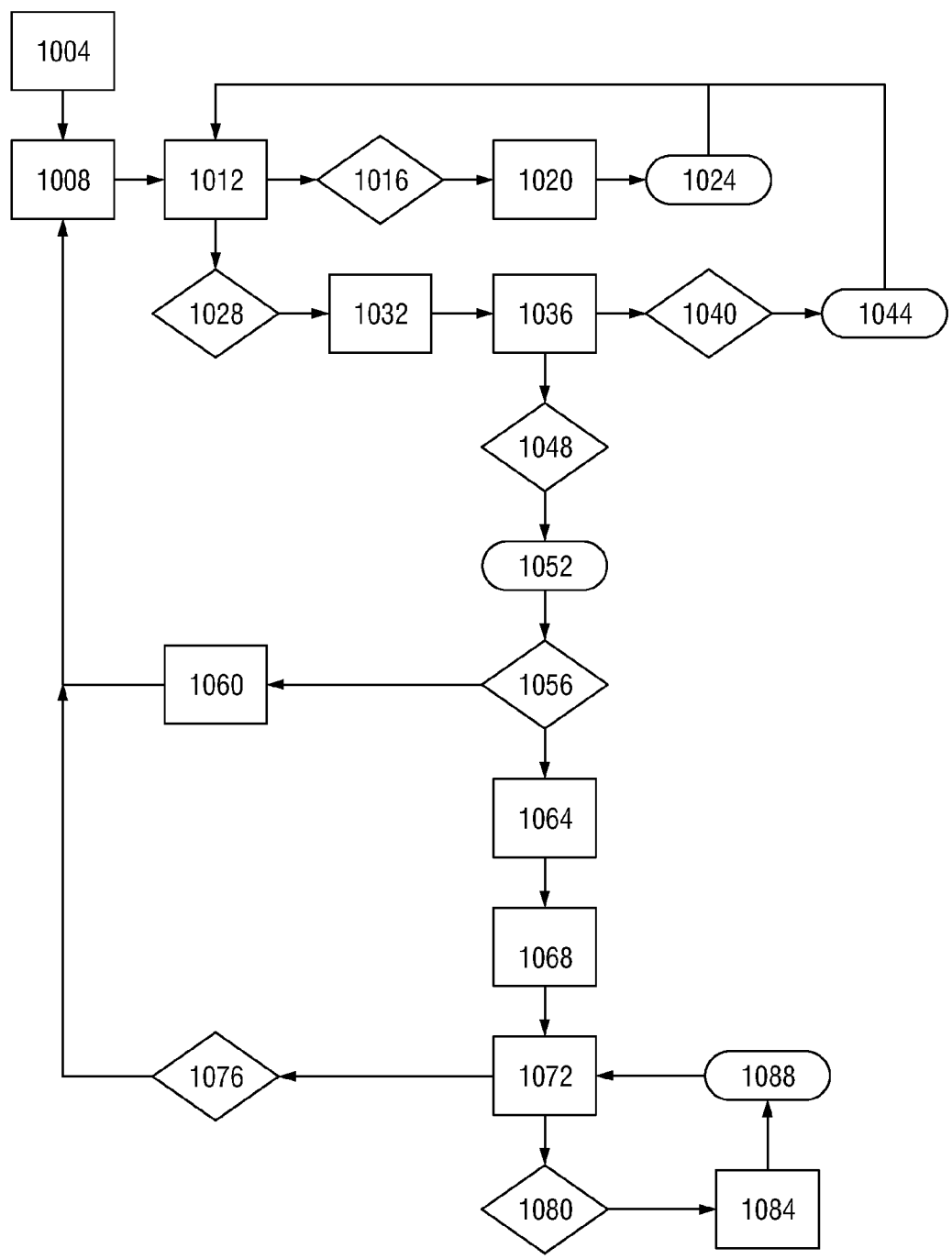
FIG. 13 is a block diagram illustrating an exemplary algorithm for device operation.

In a second non-limiting example, a hand held battery powered device 10 as depicted in FIG. 10 operationally configured to prevent unintended emission of radiant energy there from is provided. The device 10 is programmed to include a single dose activation of radiant energy emission whereby pulling and releasing the two-way trigger 52 is effective to activate the energy source 18 only if the sensor means 16 of the device 10 has sensed the target surface to within a preprogrammed distance between the sensor means 16 and the target surface, i.e., the active zone. Once the sensor means 16 reaches the active zone, a user operator of the device 10 may pull or otherwise depress the trigger 52 to activate the energy source 18 to provide a single radiant dose to the target surface. With reference to FIG. 13, an algorithm for this embodiment of operation is explained in Table 1 below.

TABLE 1

| | |
|---|---|
| 1004 | Device turned ON, Ready for Use, Start Algorithm |
| 1008 | Trigger Mechanism Disabled |
| 1012 | Does sensor detect target surface? |
| 1016 | No |
| 1020 | Trigger Mechanism Disabled |
| 1024 | No energetic transmission allowed |
| 1028 | Yes |
| 1032 | Trigger Mechanism Enabled |
| 1036 | Is Trigger Mechanism Activated? |
| 1040 | No |
| 1044 | No Energetic Transmission |
| 1048 | Yes |
| 1052 | Energetic Transmission Issued |
| 1056 | Or |
| 1060 | "Continuous Target Surface Detection" Option set to ON |
| 1064 | "Continuous Target Surface Detection" Option set to OFF |
| 1068 | Trigger Mechanism Disabled |
| 1072 | Does sensor detect absence of target surface after energetic transmission issued? |
| 1076 | Yes |
| 1080 | No |
| 1084 | Trigger Mechanism remains disabled |
| 1088 | No energetic transmission possible |

EXAMPLE 3

Figure 14:
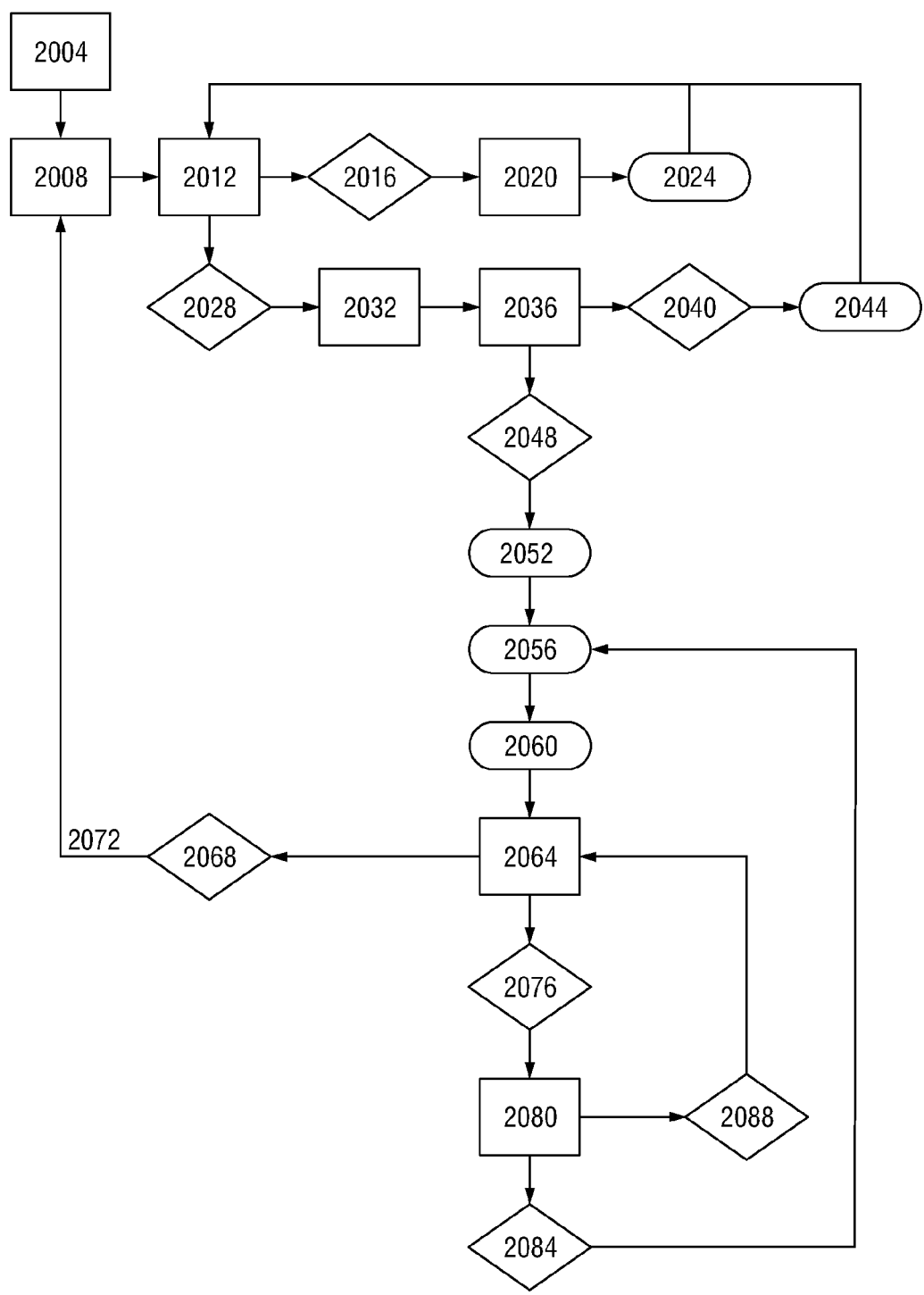
FIG. 14 is a block diagram illustrating an exemplary algorithm for device operation.

In a third non-limiting example, a hand held battery powered device 10 as depicted in FIG. 10 operationally configured to prevent unintended emission of radiant energy there from is provided. The device 10 is programmed to include an auto-dosage-sequence of radiant energy emission that continues once initiated via a single trigger 52 activation until a user operator of the device 10 once again pulls the trigger 52 to stop or pause device 10 operation. This embodiment of auto-dosage-sequence is suitably effective to prevent or reduce operator strain, e.g., hands and/or wrist strain. As shown in FIG. 11, the device 10 is suitably disabled while the sensor means 16 housed within the device 10 is located in an inactive zone. With reference to FIG. 14, an algorithm for this embodiment of operation is explained in Table 2 below.

TABLE 2

| | |
|---|---|
| 2004 | Device turned ON, Ready for Use "Automatic Energetic Transmission Sequence" turned ON Start Algorithm |
| 2008 | Trigger Mechanism Disabled |
| 2012 | Does sensor detect target surface? |
| 2016 | No |
| 2020 | Trigger Mechanism Disabled |
| 2024 | Automatic Sequence does not start |
| 2028 | Yes |
| 2032 | Trigger Mechanism Enabled |
| 2036 | Is Trigger Mechanism Activated? |
| 2040 | No |
| 2044 | Automatic Sequence does not start |
| 2048 | Yes |
| 2052 | Automatic Sequence Initiated |
| 2056 | Energetic Transmission Delivered |
| 2060 | Preset Intra-Dosage Pause |
| 2064 | Is Trigger Mechanism Activated? |
| 2068 | Yes |
| 2072 | Automatic Sequence Paused As Safety Feature |
| 2076 | No |
| 2080 | Does sensor detect target surface? |
| 2084 | Yes |
| 2088 | No |

EXAMPLE 4

Figure 15:
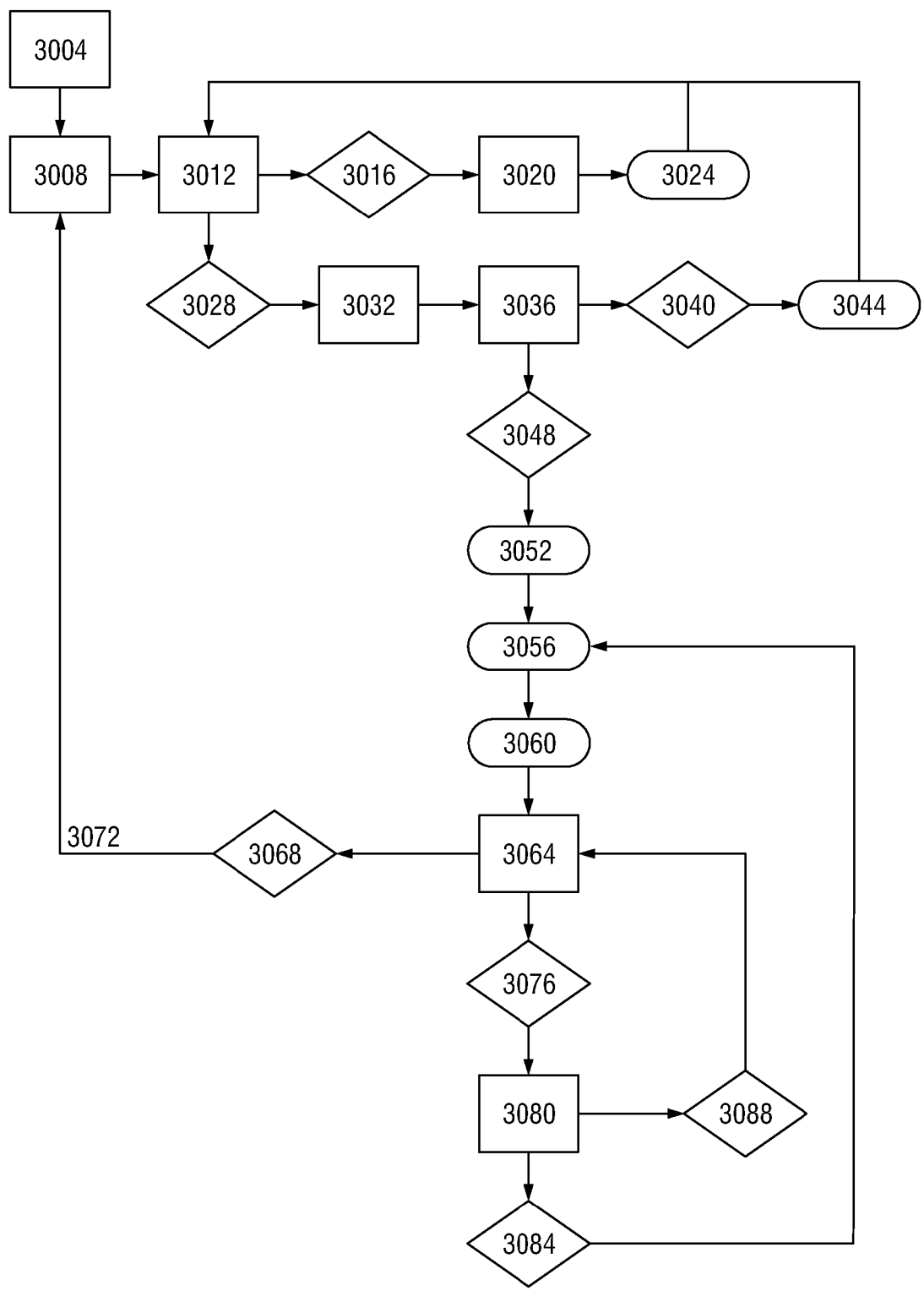
FIG. 15 is a block diagram illustrating an exemplary algorithm for device operation.

In a fourth non-limiting example, a hand held battery powered device 10 as depicted in FIG. 10 operationally configured to prevent unintended emission of radiant energy there from is provided. The device 10 is programmed to include an auto-dosage-sequence of radiant energy emission whereby the trigger 52 must be depressed and maintained in a depressed state in order to maintain energy source 18 activation, whereby release of the trigger 52 is effective to deactivate the energy source 18. In order to activate the energy source 18, a sensor means 16 within the device 10 must draw within a preprogrammed active zone. With reference to FIG. 15, an algorithm for this embodiment of operation is explained in Table 3 below.

TABLE 3

| | |
|---|---|
| 3004 | Device turned ON, Ready for Use "Automatic Energetic Transmission Sequence" turned ON Start Algorithm |
| 3008 | Trigger Mechanism Disabled |
| 3012 | Does sensor detect target surface? |
| 3016 | No |
| 3020 | Trigger Mechanism Disabled |
| 3024 | Automatic Sequence does not start |
| 3028 | Yes |
| 3032 | Trigger Mechanism Enabled |
| 3036 | Is Trigger Mechanism Activated? |
| 3040 | No |
| 3044 | Automatic Sequence does not start |
| 3048 | Yes |
| 3052 | Automatic Sequence Initiated |
| 3056 | Energetic Transmission Delivered |
| 3060 | Preset Intra-Dosage Pause |
| 3064 | Is Trigger Mechanism Activated? |
| 3068 | No |
| 3072 | Automatic Sequence Paused As Safety Feature |
| 3076 | Yes |
| 3080 | Does sensor detect target surface? |
| 3084 | Yes |
| 3088 | No |

EXAMPLE 5

In a fifth non-limiting example, a hand held battery powered device 10 as depicted in FIG. 10 operationally configured to prevent unintended emission of radiant energy there from is provided. A device 10 constructed from a rigid plastic by a molding process is provided. With reference to FIG. 16, the device 10 is described as follows:

| | |
|---|---|
| D1: | about 19.69 cm (about 7.75 inches) |
| D2: | about 12.07 cm (about 4.75 inches) |
| D3: | about 8.26 cm (about 3.25 inches) |
| D4: | about 8.26 cm (about 3.25 inches) |
| D5: | about 10.16 cm (about 4.00 inches) |
| D6: | about 8.89 cm (about 3.50 inches) |
| D7: | about 5.08 cm (about 2.00 inches) |
| D8: | about 2.54 cm (about 1.00 inches) |
| Total Weight: | about 680 grams (about 24 ounces) |

Persons of ordinary skill in the art will recognize that many modifications may be made to the present application without departing from the spirit and scope of the application. The embodiment(s) described herein are meant to be illustrative only and should not be taken as limiting the invention, which is defined in the claims.

We claim:

1. A radiant energy emitting device, comprising:
   an outer housing including at least one aperture there through, the housing being operationally configured to (1) receive and contain radiant energy therein, and (2) emit radiant energy out through the aperture to a target surface;
   an energy emission means; and
   a sensor means disposed along the entire perimeter of the aperture of the housing, the sensor means being in communication with the energy emission means and operationally configured to detect the spatial relationship between the sensor means and the target surface along the perimeter of the aperture,
   said spatial relationship determining activation of the energy emission means.

2. The device of claim 1, wherein the sensor means includes a projected field sensor.

3. The device of claim 2, wherein the sensor means is a projected capacitive sensor.

4. The device of claim 2, wherein the sensor means is operationally configured to detect the target surface through a non-electrically conductive medium.

5. The device of claim 2, wherein the sensor means is a continuous sensor having a void there through.

6. The device of claim 2, wherein the sensor means is operationally configured to allow for passage of radiant energy there through.

7. The device of claim 1, wherein the sensor means includes a proximity sensor.

8. The device of claim 1, wherein the sensor means is a continuous sensor having a void there through.

9. The device of claim 8, wherein the perimeter of the void is about equal in length to the perimeter of the aperture.

10. The device of claim 1, further comprising a manual energy activation means for activating energy emission of the device.

11. The device of claim 1, wherein the sensor means is operationally configured for unattenuated radiant energy emission during device operation.

12. The device of claim 1, including a pistol-type grip having, a trigger means for activating energy emission of the device.

13. The device of claim 1, wherein the device is operationally configured to receive radiant energy from light-emitting diodes.

14. A device for emitting radiant energy onto a target surface, comprising:
   an outer housing including at least one aperture there through;
   an energy source for generating radiant energy, the energy source being in communication with the housing;
   an activation means in communication with the energy source; and
   a sensor means disposed along the entire perimeter of the aperture of the housing, the sensor means being in communication with the activation means and operationally configured to detect the spatial relationship between the sensor means and the target surface along the perimeter of the aperture, said spatial relationship determining, operation of the activation means; wherein the housing is operationally configured to emit radiant energy out through the aperture to the target surface.

15. The device of claim 14, wherein the sensor means includes a projected held sensor.

16. The device of claim 15, wherein the sensor means is operationally configured to detect the target surface through a non-electrically conductive medium.

17. The device of claim 14, wherein the radiant energy has a wavelength from about 10 nm to about 400 nm.

18. A method for delivering radiant energy to a target surface while preventing unintended radiant energy emission, comprising:

providing a radiant, energy emitting device, comprising (A) an outer housing including at least one aperture there through, the housing being operationally configured to (1) receive and contain radiant energy therein, and (2) emit radiant energy out through the aperture to a target surface;

(8) an energy emission means; and (C) a sensor means disposed about the entire aperture of the housing, the sensor means being in communication with the energy emission means and operationally configured to detect the spatial relationship between the sensor means and the target surface 360 degrees along the perimeter of the aperture, said spatial relationship determining activation of the energy emission means;

directing the device toward a target surface until the sensor means detects the spatial relationship between the sensor means and the target surface; and activating the energy emission means for delivering radiant energy to the target surface.

19. The method of claim 18 wherein the radiant energy is provided by light-emitting diodes.

20. The method of claim 18 wherein radiant energy is delivered in an auto-dosage-sequence.

21. The method of claim 18 wherein the sensor means includes a projected field sensor.

* * * * *